United States Patent [19]

Blount

[11] 4,156,060

[45] * May 22, 1979

[54] PROCESS FOR THE PRODUCTION OF POLY (URETHANE SILICATE) PREPOLYMERS AND CELLULAR SOLID REACTION PRODUCTS UTILIZING PHENOL SILICATE COMPOUNDS AND RESINOUS PRODUCTS

[76] Inventor: David H. Blount, 5450 Lea St., San Diego, Calif. 92105

[ * ] Notice: The portion of the term of this patent subsequent to Nov. 14, 1995, has been disclaimed.

[21] Appl. No.: 875,285

[22] Filed: Feb. 6, 1978

Related U.S. Application Data

[63] Continuation-in-part of Ser. No. 747,873, Dec. 6, 1976, Pat. No. 4,094,825, which is a continuation-in-part of Ser. No. 672,559, Mar. 31, 1976, Pat. No. 4,032,511, which is a continuation-in-part of Ser. No. 555,078, Mar. 3, 1975, abandoned.

[51] Int. Cl.² ............................................. C08J 9/00
[52] U.S. Cl. ........................... 521/154; 260/18 TN; 260/824 R; 521/99; 521/104; 521/110; 521/120; 521/122; 521/125; 521/126; 521/130; 521/131; 521/137; 521/155; 521/170; 521/175; 528/44; 528/48; 528/57; 528/75; 528/76; 528/80
[58] Field of Search ........... 260/2 S, 2.5 AC, 2.5 AB, 260/2.5 AM, 77.5 AB, 77.5 AC, 77.5 AP, 77.5 CR, 18 TN, 824 R; 521/99, 110, 120, 122, 125, 137, 154, 155, 170, 175, 174, 104, 126, 131, 132, 130; 528/44, 48, 57, 75, 76, 80

[56] References Cited

U.S. PATENT DOCUMENTS 4,032,511  6/1977  Blount ............................ 260/46.5 R

OTHER PUBLICATIONS

The Merk Index, p. 1888, 1976, 9th Edition, Merk and Co. Inc. Rahway, N. J.

Primary Examiner—Melvyn I. Marquis

[57] ABSTRACT

Phenol silicate compounds and resinous products with free hydroxyl and silicate groups will react chemically with polyisocyanate compounds to produce poly (urethane silicate) prepolymers and may be cured by use of water to produce a solid/cellular solid reaction product.

12 Claims, No Drawings

4,156,060

PROCESS FOR THE PRODUCTION OF POLY (URETHANE SILICATE) PREPOLYMERS AND CELLULAR SOLID REACTION PRODUCTS UTILIZING PHENOL SILICATE COMPOUNDS AND RESINOUS PRODUCTS

CROSS-REFERENCE TO RELATED CO-PENDING APPLICATION

This Application is a continuation-in-part of U.S. Pat. application Ser. No. 747,873, filed Dec. 6, 1976, now U.S. Pat. No. 4,094,825 which is a continuation in part of U.S. Pat. application Ser. No. 672,559, filed Mar. 31, 1976, now U.S. Pat. No. 4,032,511 which is a continuation in part of U.S. Pat. application Ser. No. 555,078, filed Mar. 3, 1975, now abandoned.

BACKGROUND OF THE INVENTION

This invention relates to a process for the production of poly (urethane silicate) prepolymers and cellular solid reaction products utilizing poly (phenol silicate) resinous products. The phenol silicate compounds are produced by heating a silicon acid with a phenol in the presence of an alkali catalyst. The phenol silicate compounds will chemically react with aldehydes, diisocyanates, dicarboxyl acids and anhydrides, ketones, epihalohydrins, epoxy compounds and furans to produce useful resinous products.

The phenol silicate compounds will react with aldehyde compounds to produce poly (aldehyde phenol silicate) resinous product with free hydroxyl and silicate groups which may be reacted with polyisocyanate compounds to produce useful solid/cellular solid reaction products (poly (urethane silicate) resinous products).

The poly (urethane silicate) solid/cellular solid products may be utilized as thermal insulating material, sound proofing material, shock-resisting packaging, adhesives, casting material, constructional components of a building, and solution of poly (urethane silicate) reaction products may be used as coating agents for wood and as adhesives.

SUMMARY OF THE INVENTION

I have discovered that novel poly (urethane silicate) solid/cellular solid reaction products may be produced by chemically reacting phenol silicate compounds and poly (aldehyde phenol silicate) resinous products with polyisocyanates and isocyanateterminated polyurethane prepolymers.

Various silica compounds such as hydrated silica, hydrated silica containing Si-H bonds and silica may be used to produce phenol silicate compounds.

Any suitable phenol compound may be used in my novel process. Typical phenols include phenol, m-cresol, p-cresol, o-cresol, xylenols, resorcinol, cashew nut shell liquids, anacardol, p-tert-butyl phenol, p-tert-amyl phenol, p-phenyl phenol, anacardic acid, Bisphenol A, creosote oil, chlorophenol, nitrophenol, hydroquinone, pyrogallol, naphthol and mixtures thereof.

Any suitable alkali catalyst may be used to promote the reaction between silicon acids and phenol compounds. Typical alkali includes alkali metal carbonates, hydroxides, oxides and salts of weak acids. The preferred catalysts are sodium carbonates and sodium hydroxide.

Various aldehydes may be used to produce poly (aldehyde phenol silicate) resinous products such as formaldehyde, acetaldehyde, butylaldehyde, chloral, acrolein, paraformaldehyde, furfural, crotonaldehyde and mixtures thereof.

Various catalysts may be used to enhance the reaction between the phenol compounds and aldehydes. They may be acidic, basic or neutral. Some of the acid catalysts which may be used are mineral acids, sodium hydrogen sulfate, formic acid, acetic acid, oxalic acid, tartaric acid and aromatic sulfonic acids. Some of the basic catalysts are sodium carbonate, sodium silicate, ammonia, sodium hydroxide, potassium hydroxide, calcium hydroxide, urea and quaternary ammonium hydroxide. The aldehyde may be used in the ratio of 1 to 5 mols to each mol of the phenol silicate compound.

The cured products produced by the chemical reaction of phenol silicate compounds or poly (aldehyde phenol silicate) resinous product with polyisocyanate compounds or isocyanate-terminated polyurethane prepolymer may be quite varied in physical properties; they may be solid or porous, rigid, or elastomeric, and the porous products may be rigid or soft and flexible.

Any suitable polyisocyanate may be used in this process, for example:

1. arylene polyisocyanates such as:
    tolylene diisocyanate
    methaphenylene diisocyanate
    4-chlorophenylene-1,3-diisocyanate
    methylene-bis-(phenylene-4-)diisocyanate
    diphenylene-4,4'-diisocyanate
    3,3'-dimethoxy-biphenylene-4,4'-diisocyanate
    3,3'-diphenyldiphenylene-4,4'-diisocyanate
    naphthalene-1,5-diisocyanate
    tetrahydronaphthalene-1,5-diisocyanate
    triphenylmethane triisocyanate
2. alkylene polyisocyanates such as:
    ethylene diisocyanate
    ethylidene diisocyanate
    propylene-1,2-diisocyanate
    butylene-1,4-diisocyanate
    butylene-1,3-diisocyanate
    hexylene-1,6-diisocyanate
    decamethylene-1,10-diisocyanate
    cyclohexylene-1,2-diisocyanate
    cyclohexylene-1,4diisocyanate
    methylene-bis-(cyclohexyl-4,4'-)diisocyanate.
    Phosgenation products of aniline-formaldehyde condensation may be used. Polyisothiocyanate, inorganic polyisothiocyanates, polyisocyanates which contain carbodiimide groups, as described in German Pat. No. 1,092,007, and polyisocyanates which contain urethane groups, allophanate groups, isocyanurate groups, urea groups, imide groups or biuret groups may also be used. Toluene diisocyanate is the preferred polyisocyanate.

Any suitable isocyanate-terminated liquid polyurethane prepolymers may be used in this process, for example, the isocyanateterminated liquid polyurethane made by reacting organic polyisocyanates in molar excess with hydroxyl containing or carboxylcontaining polyesters, polyethers, polysulfides, polybutadienes, butadiene-acrylonitrite copolymers and butadiene-styrene copolymers, polyepichlorohydrin, polythioethers, polyester amides, polyacetals, urea formaldehyde resins, polycarbonates and other polyols. The process to produce the isocyanate-terminated liquid polyurethane prepolymers are well known in the arts.

Plasticizers, fillers, curing rate modifers, pigments, extender and the like may be added to the polyurethane prepolymer or may be added at the time of curing and may be in the amount from 5% to 50% by weight, based on the prepolymer. Plasticizers may include benzoate ester, phthalate esters, dipropylene glycol benzoate, dodecyl phthalate and propylene glycol phthalate. Extenders such as high boiling coal tar distillates, mineral oil, poly (alpha-methyl styrene) polymers, mercapto-terminated liquid polysulfide polymers, paraffin oil and sulphonated castor oil may be used. Finely divided fillers such as alkali metal silicates, alkaline earth metal silicates, ammonium silicate metal oxides, metal hydroxides, metal carbonates, chalk, heavy spar, gypsum, anhydrite, clay, kaolin, silica and mixtures thereof may be used in this instant process.

In the production of certain foams, it is advisable to add blowing agents. These are inert liquids with boiling points ranging from −25 degree C. to 80 degree C. and preferably from −15 degree to 40 degree C. The organic blowing agents are used in quantities of from 2% to 30% by weight, based on the reaction mixture. The organic blowing agents such as acetone, ethyl acetate, methanol, ethanol, halogenated alkanes, e.g. methylene chloride, chloroform, ethylidene chloride, vinylidene chloride, monofluorotrichloromethane, chlorodifluoromethane, dichlorodifluoromethane, butane, hexane, heptane diethylether, compounds which decompose at temperatures above room temperature with liberation of gases, e.g. nitrogen, such as azo compounds and azoisobutyric acid nitrile, may be used in this process.

Polyols may be added to the phenol silicate compounds or resinous products before the polyisocyanate is added, or they may be added to the poly (urethane silicate) propolymer in the amount of 0.5 to 2 parts by weight for each 2 parts by weight of the phenol silicate compound or resinous product.

Various polyols may be used such as glycexol glycerol monochlorohydrin, ethylene glycol, propylene glycol, butylene glycol, trimethylene glycol, tetramethylene glycol, pentamethylene glycol, hexamethylene glycol, diethylene glycol, triethylene glycol, dipropylene glycol, tetraethylene glycol, polyethylene glycol, polypropylene glycol, ether glycols, Bisphenol A, resorcinol, bis (beta-hydroethyl) terephthalate, 2-ethyl-2-(hydroxymethyl)-1,3-propanediol, pentaerythritol, trimethylolpropane, trimethylolethane, 2,2′-oxydiethanol, glucose, mannose, fructose, molasses, cane sugar, dextrose, starches, corn syrup, maple syrup, hydroxyl containing or carboxylcontaining polyesters, polysulfides, polybutadienes, butadieneacrylonitrite copolymer, butadiene-styrene copolymer, polyepichlorohydrin, polythioethers, polyester amides, polyacetals, urea formaldehyde resins, polycarbonates and mixtures thereof.

Curing catalysts may be used to cure the poly (urethane silicate) prepolymers such as water or water combined with other catalysts which are commonly known in the arts such as tertiary amines, silaamines, basic compounds which contain nitrogen (e.g. tetraalkylammonium hydroxide), alkali metal hydroxides, alkali metal phenolates, alkali metal alcolates, hexahydrotriazines, tin organo-metallic, sodium silicate and mixtures thereof. These catalysts are generally used in a quantity of from 0.001% to 10% by weight based on the weight of the polyurethane prepolymers.

Polyols, alkali metal silicates, silica, silicon acids, sodium polysulfides may be added to the water in the amount of 10% to 50% by weight. Suitable emulsifiers and foam stabilizers may be used according to this invention. Suitable emulsifiers are, e.g. the sodium salts of ricinoleic sulphonates or of fatty acids; or salts of fatty acids with amines, e.g. oleic acid diethylamine or stearic acid diethanolamine; or alkali metal or ammonium salts of sulphonic acids and fatty acids. These additives are preferably used in quantities of from 0% to 20% by weight, based on the reaction mixtures.

Suitable foam stabilizers are mainly water-soluble polyether siloxanes and those described in U.S. Pat. No. 3,629,308. These additives are preferably used in quantities of from 0% to 20% by weight, based on the reaction mixture. Further examples of surface active additives, foam stabilizers, cell regulators, negative catalyst, stabilizers, flame retarding substances, plasticizers, dyes, fillers and fungicidal and bacteriocidal substances and details about methods of using these additives and their actions may be found in Kunststoff-Handbuch, Volume VI, published by Vieweg and Hochtlen, Carl-Hanser-Verlag, Munich 1966, e.g. on pages 103 to 113.

The polyols may be first reacted with a fine, granular, silica compounds such as hydrated silica, hydrated silica containing Si-H bonds (silicoformic acid) and mixtures thereof to produce polyol silicates and polymers; these polyol silicates and polymers may be added simultaneously with the phenol silicate compounds or poly (aldehyde phenol silicate) resinous product to a polyisocyanate or a liquid isocyanate-terminated polyurethane prepolymers to produce a poly(urethane silicate) prepolymer.

The preferred method to produce poly (urethane silicate) cellular solid/solid reaction products is to mix one part by weight of a phenol silicate or poly (aldehyde phenol silicate) resinous product with 0.5 to 2 parts by weight of a polyisocyanate, then to agitate for 10 to 30 minutes at ambient temperature and pressure, thereby producing a poly (urethane silicate) prepolymer. Then 0.03 to 1 part by weight of a curing catalyst, such as water, is thoroughly mixed with the prepolymer. The mixture may begin to expand in 5 to 20 minutes to produce a cellular solid or the mixture may produce a non-porous solid.

The object of the present invention is to produce novel poly (urethane silicate) solid/cellular solid reaction products. Another object and advantage of the present invention is to utilize low cost and readily available material in the production of poly (urethane silicate) solid/cellular solid reaction products. Another object of the present invention is to produce polyurethane polymers with improved flame resistant properties. still a further object to provide novel relatively low cost, rigid, fine cellular, lightweight poly (urethane silicate) reaction products which may be used for structural purposes. Still another object is to produce novel poly (urethane silicate) solid/cellular solid reaction products which are soluble in organic solvents and may be utilized as coating agents for wood and metal.

DESCRIPTION OF PREFERRED EMBODIMENTS

My invention will be illustrated in greater detail by the specific examples which follow, it being understood that these preferred embodiments are illustrative of, but not limited to, procedures which may be used in the production of poly (urethane silicate) solid/cellular solid, reaction products. Parts and percentages are by weight unless otherwise indicated.

EXAMPLE I

About 1 mol of hydrated silica, 1 mol of phenol and 1% to 10% by weight of sodium carbonate, percentage based on weight of silica, are mixed then heated to just below the boiling point of phenol while agitating for 20 to 40 minutes, thereby producing a tan, granular, phenol silicate compound.

An aqueous solution of formaldehyde is added to the phenol silicate granules in the ratio of 1 to 1 mols, then heated to 65 degrees to 100 degrees C. while agitating for 10 to 90 minutes or until the desired viscosity is obtained, thereby producing a reddish colored poly (formaldehyde phenol silicate) resinous product.

About 2 mols of toluene diisocyanate (80% 2,4-isomer and 20% 2,6-isomer) are mixed with the said poly (formaldehyde phenol silicate) resinous product, a thick liquid, and agitated for 10 to 30 minutes at ambient temperature and pressure, thereby producing a polyurethane silicate prepolymer.

About 3% to 20%, by weight of water, percentage based on weight of reactants, is added to the polyurethane silicate prepolymer and agitated for 5 to 20 minutes or until the mixture begins to expand; it expands 6 to 10 times its original volume, thereby producing a poly (urethane silicate) cellular solid reaction product.

EXAMPLE II

About 2 mols of the phenol silicate as produced in Example I and 3 mols of toluene diisocyanate (80% 2,4-isomer and 20% 2,6 isomer) are agitated at ambient temperature and pressure for 10 to 30 minutes, thereby producing a liquid urethane silicate prepolymer.

About 3% by weight of water, percentage based on weight of the reactants, is mixed with the said prepolymer then agitated for 5 to 20 minutes, then heated to 50 degree C. to 80 degree C. for 3 to 10 minutes until the mixture begins to expand; it expands 6 to 10 times its original volume, thereby producing a rigid poly (urethane silicate) cellular solid reaction product.

EXAMPLE III

Cresol is mixed with a fine granular silicon acid containing S-H group (silicoformic acid) in the ratio of about 1:1 mols and about 5% by weight of potassium carbonate is added. The mixture is then heated to just below the boiling temperature of cresol while agitating at ambient pressure for 20 to 40 minutes, thereby producing brown granules of cresol silicoformate.

An aqueous solution of 37% formaldehyde is added to the granules of cresol silicoformate in the ratio of 5 to 1 mols, then dilute sulfuric acid is added until the pH is about 5 to 7, and the cresol silicoformate goes into solution. The mixture is then heated to 65 degree C. to 100 degree C. for 10 to 90 minutes or until the desired viscosity is reached. The resin separates from the water and is removed, thereby producing a poly (aldehyde phenol silicate) resinous product.

About equal parts by weight of poly (formaldehyde cresol silicate) resinous product and toluene diisocyanate are mixed then agitated for 10 to 30 minutes, thereby producing a liquid polyurethane silicate prepolymer.

A curing agent, an aqueous sodium silicate solution containing 50% by weight of solids, is added in the amount of 10% by weight, percentage based on weight of prepolymer, to the poly (formaldehyde cresol silicate) prepolymer then is mixed thoroughly; the temperature is kept between 50 degree C. to 80 degree C. and the mixture begins to expand in 5 to 20 minutes, thereby producing a rigid poly (urethane silicate) cellular solid reaction product.

EXAMPLE IV

About 1 part by weight of the cresol silicate and 2 parts by weight of toluene diisocyanate are mixed then agitated for 10 to 30 minutes, thereby producing a liquid polyurethane silicate prepolymer.

About 3% by weight of glacial acetic acid, percentage based on weight of the prepolymer, and the polyurethane silicate prepolymer are mixed then agitated for 5 to 20 minutes or until the mixture begins to expand, thereby producing a rigid poly (urethane silicate) cellular solid reaction product.

EXAMPLE V

About 2 mols of fine granular hydrated silica, 1 mol of resorcinol and 10% by weight of sodium carbonate, percentage based on weight of hydrated silica, are mixed then heated to just below the boiling temperature of resorcinol while agitating at ambient pressure for 20 to 40 minutes, thereby producing a mixture of resorcinol silicate and resorcinol disilicate.

To this mixture about 4 mols of an aqueous solution of formaldehyde is added then heated to 65 degree C. to 100 degree C. while agitating for 10 to 90 minutes until the desired viscosity is obtained, thereby producing poly (formaldehyde resorcinol silicate) resinous product.

About equal parts by weight of the poly (formaldehyde resorcinol silicate) resinous product and toluene diisocyanate are mixed then agitated for 10 to 30 minutes, thereby producing a polyurethane silicate prepolymer.

About 1% to 3% by weight of glacial acetic acid, percentage based on weight of the prepolymer, is added to the polyurethane silicate prepolymer and thoroughly mixed. The mixture expands 6 to 10 times its original volume, thereby producing a rigid, self standing poly (urethane silicate) cellular solid reaction product.

EXAMPLE VI

About equal parts by weight of fine grannular hydrated silica and creosote oil are mixed; then 10% by weight of dry granular sodium metasilicate granules, percentage based on the weight of the reactants are added. The mixture is then heated to just below the boiling temperature of creosote oil while agitating at ambient pressure for 20 to 40 minutes, thereby producing brown granules of creosote silicate.

About one part by weight of the creosote silicate and 2 parts by weight of an aqueous solution containing about 37% formaldehyde by weight are mixed then heated to 65 degree to 100 degree C. while agitating at ambient pressure for 10 to 90 minutes until the desireable viscosity is obtained, thereby producing poly (formaldehyde creosote silicate) resinous product.

About equal parts by weight of the liquid poly (formaldehyde cresosote silicate) resinous product and toluene diisocyanate are mixed then agitated for 10 to 30 minutes, thereby producing polyurethane silicate prepolymer.

About 3% water, containing 10% by weight of diethylenetriamine, is added to the polyurethane silicate prepolymer and thoroughly mixed; then the temperature is kept between 50 degree to 80 degree C. for 5 to 20 minutes; and the mixture expands 6 to 10 times its original volume, thereby producing a rigid poly (urethane silicate) cellular solid reaction product.

EXAMPLE VII

About 2 parts by weight of cresylic acid and 1 part by weight of fine granular hydrated silica are mixed; then 10% by weight of sodium carbonate, percentage based on the weight of the hydrated silica, is added. The mixture is then heated to just below the boiling temperature of cresylic acid while agitating for 20 to 40 minutes, thereby producing a brown granular mixture of phenol silicate and cresol silicate.

About 2 parts by weight of the mixture of phenol silicate and cresol silicate and 3 parts by weight of toluene diisocyanate are mixed then agitated for 10 to 30 minutes, thereby producing polyurethane silicate prepolymer.

About 5% by weight of water containing 10% by weight of tin octoate is added to the polyurethane silicate prepolymer and thoroughly mixed while keeping the temperature between 50 degree C. to 80 degree C. for 5 to 20 minutes or until the mixture expands, thereby producing rigid poly (urethane silicate) cellular solid reaction product.

EXAMPLE VIII

About 1 mol of the phenol silicate granules as produced in Example I, and 1 mol of furfural are mixed, then heated to just below the boiling temperature of furfural while agitating for 10 to 90 minutes, thereby producing a brown liquid, poly (furfural phenol silicate) resinous product.

About 2 parts by weight of the brown liquid poly (furfural phenol silicate) resinous product and 1 part by weight of toluene diisocyanate are mixed then agitated for 10 to 30 minutes, thereby producing polyurethane silicate prepolymer.

About 5% by weight of water is added to the prepolymer then mixed thoroughly, and the temperature is kept between 50 degree C. to 80 degree C. for 5 to 20 minutes, the mixture begins to expand. It expands 6 to 10 times its original volume, thereby producing a rigid poly (urethane silicate) cellular solid.

EXAMPLE IX

About 2 parts by weight of the mixture of resorcinol silicate and resorcinol disilicate as produced in Example V and 2 parts by weight of acrolein are mixed then heated to just below the boiling temperature of acrolein while agitating for 10 to 90 minutes, thereby producing a liquid poly (acrolein resorcinol silicate) resinous product.

About 2 parts by weight of toluene diisocyanate and 3 parts by weight of poly (acrolein resorcinol silicate) resinous product are agitated at ambient temperature for 10 to 30 minutes, thereby producing polyurethane silicate prepolymer.

About 3% by weight of glacial acetic acid is mixed thoroughly with the prepolymer and in 5 to 20 minutes the mixture begins to expand, thereby producing a rigid poly (urethane silicate) cellular solid.

EXAMPLE X

About 2 parts by weight of the phenol silicate as produced in Example I, 3 parts by weight of crotonaldehyde and 6 parts by weight of water are mixed then heated to just below the boiling point of crotonaldehyde for 10 to 90 minutes, thereby producing poly (croton-aldehyde phenol silicate) resinous product.

About 2 parts by weight of poly (croton-aldehyde phenol silicate) resinous product, 2 parts by weight of glycerol and 3 parts by weight of toluene diisocyanate are mixed then agitated at ambient temperature for 10 to 30 minutes, thereby producing a liquid polyurethane silicate prepolymer.

EXAMPLE XI

About 2 parts by weight of phenol silicate as produced in Example I and 1 part by weight of propylene glycol are mixed; then 3 parts by weight of toluene diisocyanate are added. The mixture is then agitated at ambient pressure for 10 to 30 minutes, thereby producing a liquid polyurethane silicate prepolymer. About 5% by weight of water containing 20% magnesium hydroxide is added to the prepolymer and thoroughly mixed, and the temperature is kept between 50 degree to 80 degree C. for 5 to 20 minutes; the mixture expands to 6 to 10 times its original volume, thereby producing a rigid, poly (urethane silicate) cellular solid reaction product.

EXAMPLE XII

About 2 parts by weight of cresol silicoformate as produced in Example III and 3 parts by weight of a liquid polyester produced by reacting 2 mols of maleic anhydride and 3 mols of ethylene glycol are mixed; then equal parts by weight of toluene diisocyanate are added. The mixture is agitated at ambient temperature and pressure for 10 to 30 minutes, thereby producing polyurethane silicate prepolymer.

About 3% by weight of glycial acetic acid is thoroughly mixed with the prepolymer, and in 5 to 20 minutes the mixture expands 6 to 10 times its original volume, thereby producing a rigid poly (urethane silicate) cellular solid reaction product.

EXAMPLE XIII

About 2 parts by weight of resorcinol silicate and resorcinol disilicate as produced in Example V, 0.5 parts by weight of castor oil and 2 parts by weight of toluene diisocyanate are mixed then agitated at ambient temperature and pressure for 10 to 30 minutes, thereby producing a liquid polyurethane silicate prepolymer.

About 5% dilute acetic acid is thoroughly mixed with the prepolymer, and in 5 to 20 minutes the prepolymer expands 6 to 10 times its original volume, thereby producing a rigid poly (urethane silicate) cellular solid reaction product.

EXAMPLE XIV

About 1 part by weight of liquid poly (formaldehyde phenol silicate) resinous product as produced in Example I and 2 parts by weight of a liquid isocyanate-terminated polyurethane prepolymer, containing equal parts by weight of toluene diisocyanate and castor oil, are mixed then agitated for 10 to 30 minutes. A curing agent, water containing 0.01% stannous octoate, 0.02% triethylenediamine, 5% sulphanated castor oil, 2% ammonium oleate and 0.5% paraffin oil, is added in the amount of 0.05 parts by weight to the prepolymer then thoroughly mixed. In 5 to 20 minutes the mixture expands 6 to 10 times its original volume, thereby producing a rigid poly (urethane silicate) cellular solid reaction product.

EXAMPLE XV

About 2 parts by weight of liquid poly (furfural phenol silicate) resinous product and 3 parts by weight of a liquid isocyanateterminated polyurethane prepolymer, produced by reacting polypropylene glycol (450 to 500 mol. wt.) with toluene diisocyanate in an NCO/OH molar ratio of about 2 to 1, are mixed then agitated at ambient temperature and pressure, thereby producing a polyurethane silicate prepolymer.

A curing agent, an aqueous suspension of fine granular silica containing 10% solids, is added in the amount of 10% by weight to the prepolymer and thoroughly mixed. $I_n$ 5 to 20 minutes the mixture expands 6 to 10 times its original volume to produce a rigid poly urethane silicate) cellular solid reaction product.

EXAMPLE XVI

About 1 part by weight of a liquid poly (formaldehyde creosote silicate) resinous product, and 2 parts by weight of a polyurethane prepolymer, produced by reacting a liquid hydroxyl-terminated polybutadiene with 2,4-tolylene diisocyanate and which has a free NCO content of about 6%, are mixed thoroughly. About 5% by weight of water is added to the mixture and mixed thoroughly; then in 1 to 12 hours an elastomer solid reaction product is produced. The product is further cured by heating at 70 degree to 80 degree C. for 3 to 4 hours.

EXAMPLE XVII

About 1 part by weight of poly (acrolein resorcinol silicate) resinous product and 2 parts by weight of a liquid isocyanateterminated polyurethane prepolymer (produced by reacting a liquid polyester containing 16 mols of adipic acid, 16 mols of diethylene glycol, 1 mol of trimethylol propane and toluene diisocyanate (80% 2,4-isomer and 2,6-isomer) in the ratio of 2 to 1) are mixed and agitated at ambient temperature and pressure for 10 to 30 minutes; then a curing agent, water in the amount of 5% by weight, percentage based on the weight of the reactants, is added and thoroughly mixed. The mixture begins to expand in 5 to 20 minutes. It expands 6 to 10 times its original volume, thereby producing a flexable poly (urethane silicate) cellular solid reaction product. The product is further cured by heating at 70 degree to 80 degree C. for 3 to 4 hours.

EXAMPLE XVIII

About 1 part by weight of poly (crotonaldehyde phenol silicate) resinous product as produced in Example X and 2 parts by weight of a liquid isocyanate-terminated polyurethane prepolymer, produced by reacting about equal weights of castor oil and toluene diisocyanate, are mixed then agitated at ambient temperature and pressure for 10 to 30 minutes, thereby producing a liquid polyurethane silicate prepolymer.

A curing agent (a mixture of 1 part by weight of water; glycerol silicate and poly (glycerol silicate) resinous product which is produced by mixing about 1 part by weight of glycerol, 1 part by weight of fine granular hydrated silica and 0.2 part by weight of sodium carbonate then heating the mixture to just below the boiling temperature of glycerol while agitating for 20 to 60 minutes) in the amount of 1 part by weight is added to the prepolymer and agitated thoroughly. The mixture begins to expand in 5 to 20 minutes; it expands 6 to 10 times its original volume, thereby producing a semi-rigid poly (urethane silicate) cellular solid reaction product.

EXAMPLE XIX

About 1 part by weight of poly (formaldehyde phenol silicate) resinous product, 0.2 part by weight of water and 2 parts by weight of a liquid isocyanate-terminated polyurethane prepolymer, produced by reacting 3 parts by weight of polypropylene glycol (400 to 500 mol wt.) with 2 parts by weight of toluene diisocyanate (Hylene TM), are thoroughly mixed, and within 5 to 20 minutes the mixture expands 6 to 10 times its original volume, thereby producing a semi-rigid poly (urethane silicate) cellular solid reaction product.

EXAMPLE XX

About 1 part by weight of poly (formaldehyde cresol silicate) resinous product and 0.5 part by weight of water containing 40% sodium silicate by weight are mixed with a liquid isocyanateterminated polyurethane prepolymer (produced by reacting a liquid polyester resin, containing 4 parts by weight of ethylene glycol, 1 part by weight of propylene glycol and equimolar amounts of adipic acid, and which has a molecular weight of about 1800, and is mixed with methylene bis-phenyl diisocyanate). The mixture is agitated for 10 to 30 minutes and cures after 4 to 12 hours to a solid, nonporous poly (urethane silicate) reaction product.

EXAMPLE XXI

About 1 part by weight of poly (formaldehyde phenol silicate) resinous product and 2 parts by weight of a liquid isocyanateterminated polyurethane prepolymer are mixed then agitated for 10 to 30 minutes; then 1 part by weight of water, 1 part by weight of propylene glycol and 1 part by weight of a liquid polysulfide polymer are added to the mixture. It is mixed thoroughly, and in a few minutes the mixture is cured, thereby producing a white, elastomer solid poly (urethane silicate) reaction product.

EXAMPLE XXII

About 2 parts by weight of a polyol silicate, propylene silicate (produced by mixing equal mols of a silicon acid, hydrated silica, propylene glycol and 10% by weight of an alkali compound, sodium carbonate, percentage based on the weight of the silicon acid; then the mixture is heated to just below the boiling temperature of the polyol while agitating for 20 to 60 minutes) and 2 parts by weight of poly (formaldehyde phenol silicate) resinous product as produced in Example I are mixed. To this mixture 3 parts by weight of toluene diisocyanate are added then agitated at ambient temperature and pressure for 10 to 30 minutes, thereby producing a polyurethane silicate prepolymer.

A curing agent, water containing 10% sodium polysulfide, is added in the amount of 5% by weight, percentage based on weight of the polyurethane silicate prepolymer, and thoroughly mixed. The mixture expands in 5 to 20 minutes, thereby producing a self-standing tough, rigid poly (urethane silicate) cellular solid reaction product.

Other polyols as listed in this Specification may be used in place of propylene glycol to produce polyol silicate compounds and polymer. Other Examples may be found in U.S. Pat. application No. 765,050, filed on Feb. 2, 1977, by David H. Blount.

Although specific materials and conditions were set forth in the above Examples, these were merely illustrative of preferred embodiments of my invention. Various other compositions, such as the typical materials listed above may be used, where suitable. The reactive mixtures and products of my invention may have other agents added thereto to enhance or otherwise modify the reaction and products.

Other modifications of my invention will occur to those skilled in the art upon reading my disclosure. These are intended to be included within the scope of my invention, as defined in the appended claims.

I claim:

1. The process for the production of poly(urethane silicate) reaction products by the following steps:
   (a) admixing one part by weight of a phenol silicate compound with 0.5 to 2 parts by weight of a polyisocyanate and agitating for 10 to 30 minutes, thereby
   (b) producing a poly(urethane silicate) prepolymer;
   (c) adding a curing catalyst in the amount of 0.03 to 1 part by weight, then
   (d) mixing thoroughly, thereby
   (e) producing poly(urethane silicate) reaction product.

2. The process of claim 1 wherein the phenol silicate is produced by the following steps:
   (a) mixing 1 to 2 mols of a fine granular silica compound with 1 to 2 mols of a phenol compound:
   (b) adding an alkali catalyst equal to 1% to 10% by weight, percentage based on the weight of the silica compound:
   (c) heating said mixture to just below the boiling temperature of the phenol compound for 20 to 60 minutes while agitating at ambient pressure, thereby
   (d) producing a granular phenol silicate compound.

3. The process of claim 2 wherein the phenol compound is selected from the group consisting of phenol, p-cresol, o-cresol, m-cresol, cresylic acid, xylenols, resorcinol, cashew nut shell liquid, anacordol, p-tert-butyl phenol, anacardic acid, Bisphenol A, creosote oil, 2,6-dimethylphenol, and mixtures thereof.

4. The process of claim 2 wherein the alkali catalyst is selected from the group consisting of sodium carbonate, sodium hydroxide, potassium hydroxide, potassium carbonate and mixtures thereof.

5. The process of claim 2 wherein the silica compound is selected from the group consisting of hydrated silica and hydrated containing Si-H bonds (silicoformic acid).

6. The process of claim 1 wherein the polyisocyanate is selected from the group consisting of arylene diisocyanates, alkylene diisocyanates, triphenylmethane triisocyanate and mixtures thereof.

7. The process of claim 1 wherein the polyisocyanate is selected from the group consisting of 2, 4-toluene diisocyanate, 2,6-toluene diisocyanate and mixtures thereof.

8. The process of claim 1 wherein a polyol in the amount of 0.5 to 2 parts by weight is added in step (a) of Claim 1.

9. The process of claim 1 wherein the curing catalyst is selected from the group consisting of water, water containing 10% to 50% polyol, water containing 10% to 50% sodium polysulfide, water containing 10% to 50% sodium silicate, water containing 10% to 50% silica, water containing 0.001% to 10% tin octoate, acetic acid, water containing 0.001% to 10% tertiary amines, water containg 10% to 50% polyol silicate and mixture thereof.

10. The process of claim 1 wherein the phenol silicates are reacted with an aldehyde, selected from the group consisting of an aqueous solution of formaldehyde, acetaldehyde, butylaldehyde, chloral, acrolein, paraformaldehyde, furfural, crotonaldehyde and mixtures thereof, in a ratio of 1 mol of the phenol silicates to 1 to 5 mols of the aldehyde, thereby producing a poly (aldehyde phenol silicate resinous product and is added in step (a) of calim 1.

11. The product, poly(urethane silicate) reaction product, as produced by the process of claim 1.

12. The process of claim 1, wherein a polyol is added in step (a) of claim 1 in the amount of 0.5 to 2 parts by weight of polyol to 2 parts by weight of the phenol silicate compound.

* * * * *